United States Patent
Ripich et al.

(10) Patent No.: US 11,083,477 B2
(45) Date of Patent: Aug. 10, 2021

(54) PORTABLE VACUUM-POWERED TONGUE CLEANING DEVICE

(71) Applicant: BIO-LIFE INNOVATIONS, LLC, North Canton, OH (US)

(72) Inventors: Robert J. Ripich, Canton, OH (US); David J. Boord, North Canton, OH (US)

(73) Assignee: BIO-LIFE INNOVATIONS, LLC, North Canton, OH (US)

( * ) Notice: Subject to any disclaimer, the term of this patent is extended or adjusted under 35 U.S.C. 154(b) by 32 days.

(21) Appl. No.: 15/935,758

(22) Filed: Mar. 26, 2018

(65) Prior Publication Data

US 2018/0280047 A1  Oct. 4, 2018

Related U.S. Application Data

(60) Provisional application No. 62/476,434, filed on Mar. 24, 2017.

(51) Int. Cl.
| | |
|---|---|
| *A61B 17/24* | (2006.01) |
| *A61C 17/08* | (2006.01) |
| *A61B 17/32* | (2006.01) |
| *A61B 17/00* | (2006.01) |

(52) U.S. Cl.
CPC .. *A61B 17/244* (2013.01); *A61B 2017/00734* (2013.01); *A61B 2017/320008* (2013.01); *A61B 2217/005* (2013.01); *A61C 17/08* (2019.05); *A61M 2210/0643* (2013.01)

(58) Field of Classification Search
CPC .......... A61B 17/24; A61B 17/244; A61B 2017/320008; A61C 17/08; A61M 2205/8243; A61M 1/0086; A61M 2217/005

See application file for complete search history.

(56) References Cited

U.S. PATENT DOCUMENTS

| | | | |
|---|---|---|---|
| 1,811,775 A | 7/1930 | Barkwill | |
| 3,394,277 A * | 7/1968 | Lyons | A61C 17/40 310/80 |
| 3,768,477 A | 10/1973 | Anders et al. | |
| 3,890,964 A | 6/1975 | Castanedo | |
| 4,043,322 A | 8/1977 | Robinson | |
| 4,340,365 A | 7/1982 | Pisanu | |
| 4,538,631 A | 9/1985 | Prince | |
| 4,806,101 A | 2/1989 | Rossi | |

(Continued)

OTHER PUBLICATIONS

U.S. Pat. No. 872,567 dated Dec. 3, 1907 Langstaff.

*Primary Examiner* — Tan-Uyen T Ho
*Assistant Examiner* — Charles M Wei
(74) *Attorney, Agent, or Firm* — McDonald Hopkins LLC

(57) ABSTRACT

A portable, self-contained vacuum tongue cleaning device uses a removable cleaning head so that different heads can be used with different users. The device includes a debris and saliva separator that removes the debris and saliva from the vacuum flow. This separator is carried by the cleaning head in order to minimize required cleaning of the base of the device. The base carries a vacuum pump, a power supply, a switch, and an inlet that allows the power supply to be recharged. The device is configured for emergency use in an oral surgeon's office wherein vacuum flow is required during surgeries.

16 Claims, 4 Drawing Sheets

(56) References Cited

U.S. PATENT DOCUMENTS

| | | | |
|---|---|---|---|
| 5,133,714 A * | 7/1992 | Beane | A61B 18/1402 606/35 |
| 5,151,084 A * | 9/1992 | Khek | A61B 17/320068 604/22 |
| 5,188,402 A * | 2/1993 | Colgate | F16J 15/0881 220/304 |
| 5,282,814 A | 2/1994 | Srivastava | |
| 5,401,255 A * | 3/1995 | Sutherland | A61M 39/24 604/247 |
| 5,486,162 A * | 1/1996 | Brumbach | A61F 9/00745 604/22 |
| 5,624,259 A | 4/1997 | Heath et al. | |
| 5,779,475 A | 7/1998 | Patel | |
| 5,779,654 A | 7/1998 | Foley et al. | |
| 5,792,159 A | 8/1998 | Amin | |
| 6,015,293 A | 1/2000 | Rimkus | |
| 6,083,003 A | 7/2000 | Kwasnik et al. | |
| 6,102,923 A * | 8/2000 | Murayama | A61B 17/244 601/142 |
| 6,139,558 A | 10/2000 | Wagner | |
| 6,159,226 A | 12/2000 | Kim | |
| 6,235,039 B1 * | 5/2001 | Parkin | A61B 17/545 606/131 |
| 6,322,573 B1 | 11/2001 | Murayama | |
| 6,613,056 B1 * | 9/2003 | Brumbach | A61B 17/320068 606/128 |
| 7,029,484 B2 | 4/2006 | Ripich | |
| 7,051,394 B2 | 5/2006 | Gavney, Jr. | |
| D612,048 S | 3/2010 | Baynham | |
| 8,088,133 B2 | 1/2012 | Bosma et al. | |
| D704,835 S | 5/2014 | Hajarian et al. | |
| 8,904,590 B2 * | 12/2014 | Jungnickel | A46B 15/0002 15/105 |
| 9,138,046 B2 | 9/2015 | Jimenez et al. | |
| 9,226,764 B2 | 1/2016 | O'Neil et al. | |
| 9,265,513 B2 | 2/2016 | Ripich et al. | |
| D771,813 S | 11/2016 | Rpich et al. | |
| 2002/0108614 A1 | 8/2002 | Schultz | |
| 2003/0083680 A1 | 5/2003 | Jousson | |
| 2003/0167032 A1 * | 9/2003 | Ignon | A61B 17/545 604/19 |
| 2003/0167582 A1 * | 9/2003 | Fischer | A61B 17/244 15/22.1 |
| 2003/0186192 A1 | 10/2003 | Ito et al. | |
| 2005/0004520 A1 * | 1/2005 | Lemoine | A61M 1/0047 604/118 |
| 2005/0050676 A1 | 3/2005 | Khan | |
| 2005/0096573 A1 | 5/2005 | Liu | |
| 2009/0111069 A1 * | 4/2009 | Wagner | A61B 17/244 433/95 |
| 2009/0192442 A1 * | 7/2009 | Ignon | A61M 35/003 604/22 |
| 2011/0196365 A1 * | 8/2011 | Kim | A61B 18/18 606/33 |
| 2011/0202021 A1 * | 8/2011 | Ho | A61B 17/24 604/319 |
| 2011/0282268 A1 * | 11/2011 | Baker | A61M 3/0275 604/20 |
| 2011/0313412 A1 * | 12/2011 | Kim | A61B 18/18 606/33 |
| 2013/0090665 A1 * | 4/2013 | Linde | A61B 17/24 606/106 |
| 2014/0257173 A1 | 9/2014 | Ohanessian | |
| 2016/0256671 A1 * | 9/2016 | Ignon | A45D 34/04 |

* cited by examiner

PORTABLE VACUUM-POWERED TONGUE CLEANING DEVICE

CROSS REFERENCE TO RELATED APPLICATIONS

This application claims the benefit of U.S. Provisional Patent Application No. 62/476,434 filed Mar. 24, 2017; the disclosures of which are incorporated herein by reference.

BACKGROUND OF THE DISCLOSURE

1. Technical Field

The present disclosure generally relates to tongue cleaning devices and, more particularly, to a portable, self-contained tongue cleaning device used in cooperation with a vacuum to remove tongue debris from the tool after the tool removes the debris from the tongue.

2. Background Information

Numerous types of tongue cleaning devices are known in the art. All have advantages and disadvantages. The art generally desires a tongue cleaning device that effectively cleans the plaque and debris from the tongue while being safe, easy to use, and effective.

One drawback with existing tongue cleaning devices is that the debris collected by the device can fall off of the device shortly after the device is removed from the tongue. Most home users clean their tongues over a bathroom sink and the debris retention problem does not bother them or stop them from using the devices. In other settings, the debris retention problem is of more concern. One such setting is a hospital where it is becoming more desirable to clean the tongues of bedridden patients in order to reduce the amount of bacteria of the patient's tongue. Another situation is a surgical suite wherein the tongue of a patient is cleaned prior to anesthesia. Those who use tongue cleaning devices in these situations desire a tongue cleaning device that will retain or remove the debris from the scraping wall of the tongue cleaning device so that the tongue cleaning device may be easily used on a patient who is lying on his back.

Different vacuum solutions are known in the art for gathering debris with a vacuum flow. Most of these use a dental or surgical vacuum pump. These devices are not readily portable which prevents them from being used in situations like nursing homes wherein a nurse may wish to use the devices in all of the patients' rooms. One portable device is disclosed in FIG. 27 of US Publication 20020128673A1.

SUMMARY OF THE DISCLOSURE

The disclosure provides a portable, self-contained vacuum tongue cleaning device.

The device uses a removable and replaceable working head so a single head can be removed, cleaned, and replaced or so that different heads can be used with different users.

The device includes a debris and saliva separator that removes the debris and saliva from the vacuum flow. This separator is carried by the cleaning head in order to minimize required cleaning of the base of the device.

The device includes a base that carries a vacuum pump, a power supply, a switch, and an inlet that allows the power supply to be recharged.

The device is configured for emergency use in an oral surgeon's office wherein vacuum flow is required during surgeries.

The preceding non-limiting aspects, as well as others, are more particularly described below. A more complete understanding of the processes and equipment can be obtained by reference to the accompanying drawings, which are not intended to indicate relative size and dimensions of the assemblies or components thereof. In those drawings and the description below, like numeric designations refer to components of like function. Specific terms used in that description are intended to refer only to the particular structure of the embodiments selected for illustration in the drawings, and are not intended to define or limit the scope of the disclosure.

BRIEF DESCRIPTION OF THE DRAWINGS

Similar numbers refer to similar parts throughout the specification.

DETAILED DESCRIPTION OF THE DISCLOSURE

Figure 1:
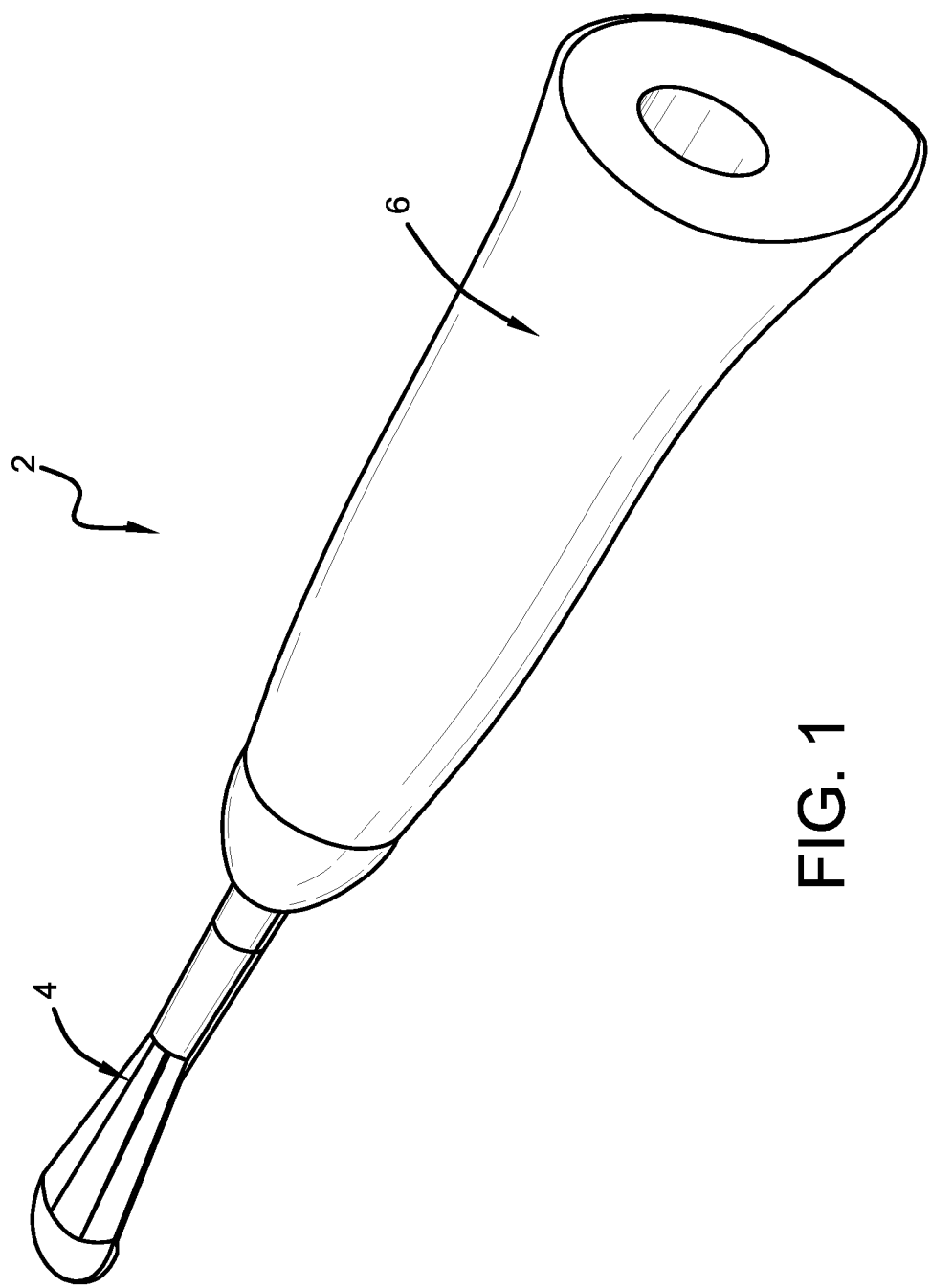
FIG. 1 is a perspective view of an exemplary configuration for the portable tongue cleaning device.
Figure 2:
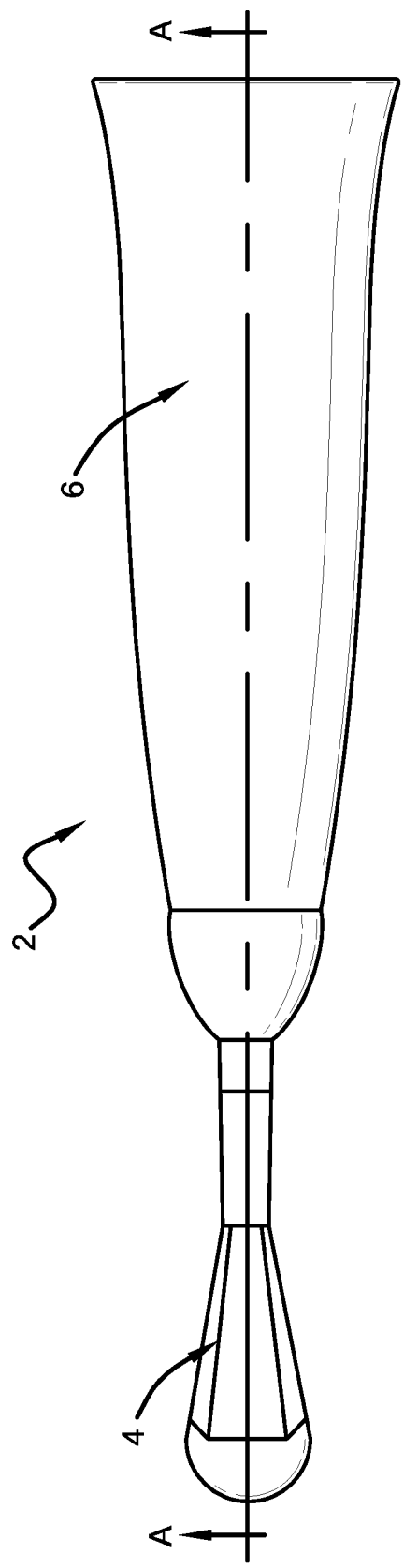
FIG. 2 is a top plan view of the device of FIG. 1.
Figure 3:
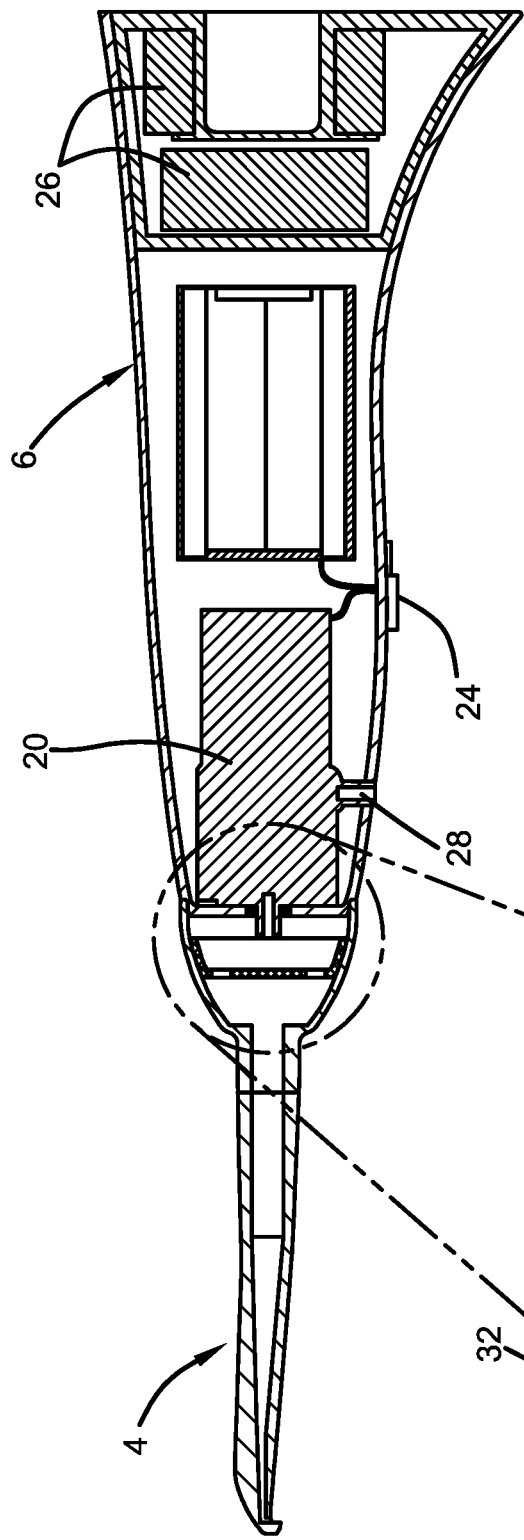
FIG. 3 is a section view taken along line A-A of FIG. 2.
Figure 4:
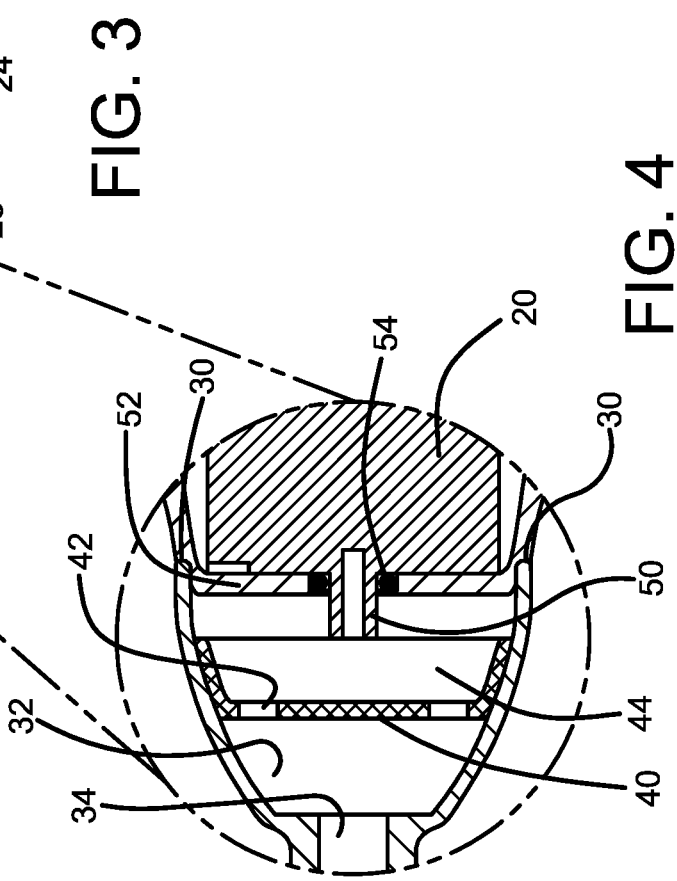
FIG. 4 is an enlarged view of the encircled portion of FIG. 3.
Figure 5:
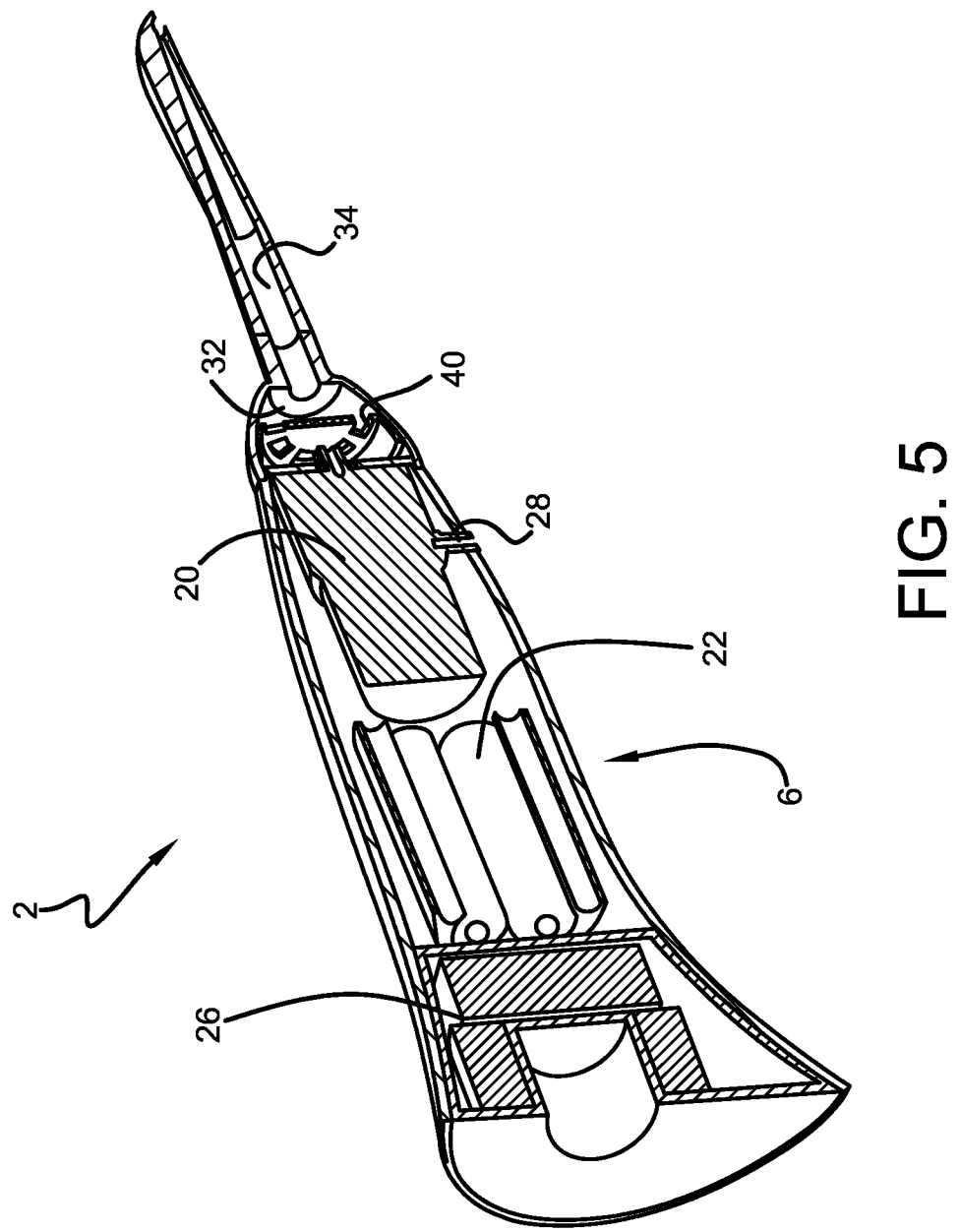
FIG. 5 is a perspective cross sectional view of the device of FIG. 1.

The exemplary configuration of the portable, self-contained vacuum powered tongue cleaning device is indicated generally by the reference numeral 2 in the accompanying drawings. Each device 2 has a removable and replaceable working head 4 that defines a vacuum passage configured to direct a vacuum flow to a working edge to remove debris from the tool after the tool has removed debris from the tongue. Exemplary structures of the tongue-engaging working edge and vacuum channel are disclosed in US Patent Publications 20020128673A1 and 20160228137A1 which are both incorporated herein by reference. In some of the exemplary configurations, a liquid such as an antibacterial solution can be applied to the tongue immediately before or after the cleaning by the working edge. Device 2 also includes a hand-held base 6 that is portable and provides the vacuum flow that is applied to working head 4. Each configuration of working head 4 can be fabricated from any of a variety of rigid materials such as moldable or printable plastics, medical device polymers, ceramics, and/or metals. Working head 4 can be fabricated from titanium. Working head 4 can be fabricated from a material that can be sterilized under high heat. In a disposable configuration, working head 4 can be made from a recyclable polymer or a paper-based material.

Base 6 has a body that carries a vacuum pump 20, a power supply 22, a switch 24, and a charging inlet 26. In this example, charging inlet 26 includes an inductive charging winding coil and a diode pack and power supply. Vacuum pump 20 includes a discharge outlet 28 that extends from the bottom of base 6.

Working head 4 is removably and replaceably connected to the front end of base 6 with a snap fit, threaded fit, bayonet fit, or friction fit that is also sealed against the leakage of gathered saliva. The seal can be provided by the snap fit between the materials themselves, an O-ring can be provided, or a resilient seal can be provided to create this seal. A friction fit is indicated by reference numeral 30. The working head 4 can be removed and then replaced or working head 4 can be removed and a new working head 4 can be replaced in its place.

At the rear end of working head 4, an effluent chamber 32 is defined by the body of working head 4. Chamber 32 is defined by an enlarged rear region of working head 4. Chamber 32 defines a portion of the vacuum flow channel and has a much larger cross sectional area than the cross sectional area of the debris and saliva channel 34 that extends from chamber 32 to the working edge of working head 4. This change in cross section causes the vacuum flow being pulled through channel 34 to slow and drop carried saliva and debris out of the vacuum flow. An increase in cross sectional area of a factor of three is an example that slows the flow enough to drop debris into chamber 32. Larger increases can be used to slow the flow more dramatically.

A baffle 40 is carried in chamber 32 which redirects the vacuum flow through at least one tortuous path to further drop saliva and debris from the vacuum flow. Baffle 40 defines at least one opening 42. The one or more opening 42 can be evenly disposed about baffle 40 or opening 42 can be disposed only at the top of baffle 40. Baffle 40 can be cup-shaped with a sidewall 44 that seals against the inner surface of the frustoconical wall that defines chamber 32. Baffle 40 can be substantially perpendicular to the longitudinal axis of device 2 or it can be tilted towards or away from the front of device 2 to increase the size of impingement surface of baffle 40. In one example, baffle 40 is tilted and opening 42 or openings 42 are only disposed in the upper half of baffle 40. In another example, multiple baffles 40 are provided with non-aligned openings 42 to create a tortuous path for the vacuum flow.

Vacuum pump 20 can use an inlet nipple 50 that extends into chamber 32 away from the front wall 52 of base 6. A seal 54 is disposed around nipple 50 and front wall 52.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the description and illustrations provided herein are examples and the invention is not limited to the exact details shown or described. Throughout the description and claims of this specification the words "comprise" and "include" as well as variations of those words, such as "comprises," "includes," "comprising," and "including" are not intended to exclude additives, components, integers, or steps.

The invention claimed is:

1. A portable, self-contained tongue cleaning device with a powered vacuum debris removal capability; the device comprising:
   a hand-held base that carries a power supply and a vacuum pump; the vacuum pump having an inlet;
   a working head having a working edge adapted to engage the tongue and remove debris from the tongue when the working edge is dragged across a portion of the tongue;
   the working head being removably and replaceably connected to the hand-held base; a portion of the working head covering the inlet of the vacuum pump when the working head is connected to the hand-held base;
   the working head defining a vacuum passage configured to direct a vacuum flow to the working edge and being adapted to remove debris from the working edge after the working edge has removed debris from the tongue;
   the vacuum passage being in fluid communication with the inlet of the vacuum pump when the working head is connected to the hand-held base; and
   the inlet of the vacuum pump is an inlet nipple that projects beyond the outer surface of the hand-held base wherein the working head defines a chamber that has a larger cross sectional area than the vacuum passage that extends from the chamber to the working edge of the working head, the inlet nipple projects into the chamber such that the inlet nipple is spaced from the working head and defines a portion of a vacuum flow channel.

2. The device of claim 1, wherein the hand-held base includes an on-off switch electrically connected to the vacuum pump.

3. The device of claim 1, wherein the power supply includes at least one rechargeable battery.

4. The device of claim 3, wherein the hand-held base defines a recess with an inductive winding coil disposed around the recess.

5. The device of claim 1, further comprising a seal between the inlet nipple and the hand-held base.

6. The device of claim 1, further comprising a baffle disposed in the chamber.

7. The device of claim 1, wherein the working head defines the chamber; the vacuum passage extending between the chamber and an end of the working head that carries the working edge.

8. The device of claim 7, further comprising a baffle disclosed in the chamber; the baffle defining at least one opening that is out of alignment with the vacuum passage and inlet of the vacuum pump to define a tortuous path for a vacuum flow passing through the chamber.

9. The device of claim 8, wherein the baffle includes a sidewall; the chamber having a frustoconical sidewall portion; the sidewall of the baffle being disposed against an inner surface of the frustoconical sidewall portion.

10. The device of claim 8, wherein the portion of the chamber disposed between the baffle and the vacuum passage is an effluent chamber adapted to retain debris removed from the working edge with the vacuum flow.

11. The device of claim 8, wherein the at least one opening defined by the baffle is disposed in a top half of the baffle.

12. The device of claim 8, wherein the baffle is tilted to provide a tilted impingement surface.

13. The device of claim 7, further comprising a plurality of spaced baffles disposed in the chamber; each of the baffles defining at least one opening wherein the openings of the plurality of spaced baffles, the inlet, and vacuum passage being disposed out of alignment to define a tortuous vacuum flow path.

14. The device of claim 1, wherein the working head is removably and replaceably connected to the hand-held base with a snap fit.

15. The device of claim 14, further comprising a seal disposed between the working head and the hand-held base.

16. The device of claim 1, wherein the working head is removably and replaceably connected to the hand-held base with a friction fit.

* * * * *